United States Patent [19]

Berger

[11] Patent Number: 4,982,597

[45] Date of Patent: Jan. 8, 1991

[54] RESTRICTOR HEATING IN SUPERCRITICAL FLUID CHROMATOGRAPHY

[75] Inventor: Terry A. Berger, Landenburg, Pa.

[73] Assignee: Hewlett-Packard Company, Palo Alto, Calif.

[21] Appl. No.: 377,534

[22] Filed: Jul. 10, 1989

Related U.S. Application Data

[63] Continuation of Ser. No. 207,336, Jun. 7, 1988, abandoned.

[51] Int. Cl.$^5$ .................... G01N 30/30; G01N 30/32
[52] U.S. Cl. .................................. 73/23.1; 73/61.10 C
[58] Field of Search .......................... 73/23.1, 61.1 C

[56] References Cited

U.S. PATENT DOCUMENTS 3,522,725  8/1970  Waters ........................... 73/61.1 C

FOREIGN PATENT DOCUMENTS 8747  1/1985  Japan ................................. 73/23.1
148855  7/1987  Japan ............................. 73/61.1 C
329467  6/1972  U.S.S.R. ......................... 73/23.1

Primary Examiner—Hezron E. Williams
Assistant Examiner—Joseph W. Roskos
Attorney, Agent, or Firm—Richard F. Schuette

[57] ABSTRACT

In a system for analyzing a chemical sample by chromatographic separation of said sample into components a method and apparatus are provided for heating the mobile phase to a desired temperature prior to exiting the restrictor, while maintaining the density of the mobile phase at a desired level. Such heating and density maintenance being provided by the combination of a restrictor having a minimal taper length and a temperature zone immediately prior to the outlet end of the restrictor, which temperature zone has a minimum length. A second temperature zone spaced upstream from the first zone, and an intermediate thermally conductive member between the first and second zones can be provided as an alternative embodiment for establishing a thermal gradient. As the mobile phase passes through the second zone, the intermediate conductive member, and the first zone, the mobile phase is subjected to a thermal gradient.

14 Claims, 5 Drawing Sheets

RESTRICTOR HEATING IN SUPERCRITICAL FLUID CHROMATOGRAPHY

This is a continuation, of application Ser. No. 207,336, filed June 7, 1988 now abandoned.

RELATED APPLICATIONS

This application relates to U.S. Pat. No. 4,845,985 entitled IMPROVED SUPERCRITICAL FLUID CHROMATOGRAPHY, which is incorporated herein by reference as if such application were reproduced in full.

FIELD OF THE INVENTION

The present invention relates to an advancement in the art of Supercritical Fluid Chromatography (SFC) and, more particularly, to a capillary SFC system, wherein a restrictor, provided at the outlet and end of the capillary, is heated.

BACKGROUND OF THE INVENTION

In analytical chemistry, liquid and gas chromatography techniques have become important tools in the identification of chemical sample components. The basic principle underlying all chromatographic techniques is the separation of a sample chemical compound into individual components by transporting the compound in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

Consider, for example, a gas chromatograph. Typically, a supply of inert carrier gas (mobile phase) is continually passed as a stream through a heated column containing porous retentive media (stationary phase). A sample of the subject compound is injected into the mobile phase stream and passed through the column. A detector, positioned by the outlet end of the column, detects each of the separated components as they exit the column. Separation is due primarily to the differential volatility and retention characteristics of each sample component as the temperature in the column is increased.

Gas chromatography detectors typically include heated zones in their base portion which pre-heat the mobile fluid prior to detection at least 50° C. above column temperature to prevent cold trapping solutes in the transfer lines between the column and the detector. In gas chromatography, dimensions of such heated zones are almost irrelevant as long as the fluid is heated sufficiently to prevent cold trapping.

The analytical choice between liquid and gas chromatography techniques is largely dependent of the molecular weight of the compound being analyzed. Liquid chromatographs are capable of analyzing much heavier compounds than gas chromatographs. However, since gas chromatography detection techniques are more sensitive, they are preferred.

The advent of Supercritical Fluid Chromatography (SFC) provided a potential bridge between gas and liquid chromatography advantages, i.e., high sensitivity and heavier molecular weight samples. In SFC, a fluid heated above the critical point, is used as the mobile phase. Such fluid is passed under pressure through a retentive media. As the pressure of the mobile phase is increased, for example, from about 40 ATM to approximately 400 ATM, the sample being analyzed separates into its various components dependent upon the relative differential solubility of each component with the mobile phase. Since the mobile phase is a gas, gas chromatography detectors can be utilized, significantly enhancing detection sensitivity. SFC can be simplistically viewed as an extension of gas chromatography to higher molecular weight components where separation is now density related rather than temperature related. SFC has been found to be primarily useful in the analysis of moderate molecular weight homologous series (M.W. 100 to 10,000) and some thermally labile molecules such as pesticides and drugs.

Originally, SFC systems used media packed columns similar to those used in gas chromatography. However, due to concerns over large pressure drops, decreased efficiency and poor media stability, the use of capillaries as the stationary phase in place of media packed columns has becomes generally accepted. SFC systems utilizing a capillary stationary phase are generally referred to as capillary SFC systems. Systems of the type will find the present invention of primary usefulness.

Consider generally the capillary SFC system. A mobile phase gas is supplied to a pump which in turn supplies the gas to an injector. The sample to be analyzed is injected into the mobile phase and the combination is supplied to a splitter. Since capillary (Stationary Phase) SFC utilizes a very small volume, typically on the order of 100 nanoliters, a splitter is incorporated to ensure that only the allowed volume of the combination is passed through the capillary for analysis. In order to maintain the temperature of the mobile phase above its critical temperature, the splitter and the capillary are placed within an oven. Since SFC is carried out under predetermined pressure conditions to effect various density changes, either static or programmed dynamic pressure conditions, a restrictor is placed at the capillary outlet and in the splitter's excess fluid output to limit mass flow. Pressure is controlled by the pump. The capillary restrictor output is passed through a detector. The output of the detector, a voltage signal, is applied to an X-Y plotter or some form of chart recorder which graphs detector output vs. time. Since pressure is also changed over time, for example, increasing the pump pressure at a fixed rate, the resulting SFC chromatiogram is also a reflection of detector output vs. pressure.

As will be understood, the splitter design and the restrictors function to create a flow ratio such that the nanoliter capillary volume is maintained. This ratio is also referred to as the split ratio.

Since SFC operates at very high pressures and gas chromatography style detectors typically operate near ambient pressure or below, a pressure reduction device must be incorporated. To prevent loss of solutes in a low pressure transfer line, the pressure reduction device should be placed inside the base of the detector so that a portion of the mobil phase expansion, which occurs as gas exits the device, takes place in the detector. Typically, the restrictor placed at the capillary outlet serves to both limit mass flow and to reduce mobile phase pressure prior to detection. The necessity for pressure reduction is also dependent on the type of detector used. For example, if a spectrofluorimetric detector is used, detection would occur prior to the restrictor.

Unfortunately, the design of the restrictor incorporated in such previous SFC systems and the manner in which such restrictors were heated has had an effect on detection efficiency. Consider first the general design characteristics of a typical restrictor which will be similar to that shown in FIG. 1. A restrictor 10, which is of generally cylindrical shape, is provided with a central bore 12 about a central axis 14. Central bore 12 at its inlet end 16 is of substantially the same diameter $D_i$ as the internal diameter of the capillary to which restrictor 10 would be attached. The outlet end 18 is of a substantially smaller diameter $D_o$ than inlet and 16. Beginning a distance $L_t$ upstream from outlet end 18, the interior surface of bore 12 converges forward towards axis 14 yielding a generally frusto conical shape. As used herein, the length $L_t$ is referred to as the taper length. Prior to the present invention, the importance of the taper length has not been appreciated.

Consider now, some specific design characteristics of known restrictors. One previous restrictor incorporated a thick wall capillary drawn down to a pinhole with a very steep taper on the internal diameter having a relatively short taper length. Appropriate dimensions are on the order of exit diameter of 0.5 to 4 $\mu$m, inlet diameter of 25 to 100 $\mu$m, outside diameter of 300 to 500 $\mu$m and taper length of 1 to 5 mm. Total length may be 10 to 20 cm. Alternatively, present restrictors have been integrally formed in an analytical capillary column, for example a drawn restrictor, having a much longer taper length.

Consider now the heating of the mobile phase flowing through above described restrictors in present SFC systems. Since the restrictor internal diameter (ID) just ahead of the taper remains the same as the restrictor inlet, the pressure in this region is the same as column pressure. When using an unmodified gas chromatography detector such as an FID for SFC detection, fluid density can decrease as much as five time as a worst case as a result of the heating caused by the FID heat zone length. This also increases fluid linear velocity as mush as five times. Such a density drop will likely cause solutes to drop out of solution and stick to the walls of the restrictor. For low volatility components the modest increase in linear velocity is unlikely to sweep such components off the restrictor walls and into the detector. The effect will be most severe for higher molecular weight, low volatility solutes which will yield distorted molecular weight distribution information such as desirable in the analysis of homologous series.

Heating restrictors is necessary because restrictors having the dimensions described above cause substantial drops in mobile phase pressure which results in substantial adiabatic cooling of the fluid. The resulting fluid temperature drop is characteristic of the molecular structure. For molecules like carbon dioxide, final temperature occurring after the fluid exits the restrictor, may reach 0.833 times initial, pre-expansion temperature. Phase transition to solid or liquid particles can occur. Such particles can entrap solute molecules and yield noisy flow and signal bursts in the detector as "snow" particles melt. Consequently, SFC detection efficiency will not reach desired levels until the above problems can be resolved.

In the tapered part of the restrictor during a heating operation, continuously decreasing ID combined with increasing temperature and decreasing pressure causes rapid increases in linear velocity. While this helps sweep solutes dropping out of solution into the detector the transit time of individual molecules across the restrictor can becomes extremely short down into the tens of microseconds, complicating heat transfer into the fluid.

The restrictor heating problem is further complicated in that the best materials of construction for restrictors are both chemically and catalytically inert. Fused silica tubing is probably the best material, however, it is also a relatively good insulator. Additionally, restrictors of the type previously described are most easily fabricated using thick wall tubing further decreasing heat transfer.

Some supercritical fluids of interest in chromatography have low critical temperatures. The required restrictor temperatures to avoid phase transitions can therefore also be quite low. It is sometimes true that this temperature is below oven temperature. Consequently, it may be desirable to cool or maintain mobile temperature in the restrictor.

In some situations such as in the use of an unmodified FID, the restrictor effluent is burned in a hydrogen-oxygen or hydrogen-air flame. Such combustion produces water vapor which depending on detector design can condense to a liquid in the exit chimney. During gas chromatography using an FID, the detector base heated zone is quite hot, up to 400° C. and is at least partially thermally coupled to the exit chimney preventing water condensation. When used with SFC, the same detectors can and are run much cooler so that water condensation is much more likely. Water droplets thus formed can run down into the detection volume causing corrosion or even extinguishing the flame. Corrosion causes noisy detector response and flame extinguishment prevents detection.

Consequently, a need still exists for a capillary SFC system which incorporates a restrictor and which heats the mobile phase passing through such restrictor, yet is capable of maintaining a high detection efficiency.

SUMMARY OF THE INVENTION

Therefore it is an object of the present invention to provide a method and apparatus for analyzing a chemical sample by chromatographic separation which incorporates a restrictor and which heats a mobile phase passing through such restrictor, yet is capable of maintaining a high detection efficiency.

It is another object of the present invention to provide a method and apparatus for analyzing a chemical sample by chromatographic separation which acts to prevent solutes from dropping out of solution prior to detection.

It is a further object of the invention to provide a method and apparatus for analyzing a chemical sample by chromatographic separation which prevents substantial adiabatic cooling of the mobile fluid.

It is a further object of the invention to provide a method and apparatus for analyzing a chemical sample by chromatographic separation which acts to prevent phase transition from occurring.

It is a further object of the invention to provide a method and apparatus for analyzing a chemical sample by chromatographic separation which effectively heats the mobile fluid prior to detection.

It is yet another object of the invention to provide a method and apparatus for analyzing a chemical sample by chromatographic separations which acts to prevent condensation from occurring in the detector.

These and other objects of the invention are achieved and previously described difficulties are overcome by a method and apparatus which heats the mobile fluid to a desired temperature prior to the fluid exiting the restrictor while maintaining the density of the mobile phase at a desired level. Such heating and density maintenance is achieved by the combination of a restrictor having a minimal taper length and a heated zone in an area immediately prior to the outlet end of the restrictor which heated zone has a minimum length. In an alternative embodiment, a second temperature zone may be provided in an area spaced up stream from the first temperature zone. The first and second zones are connected in a thermally conductive fashion so that fluid passing through the second zone, through the space in between, and through the first temperature zone, is subjected to a thermal gradient.

These and other object and advantages of the invention will become more apparent from the following detailed description when taken in conjunction with the following drawings.

DETAILED DESCRIPTION OF THE PREFERRED EMBODIMENT

As will be described with regard to the figures, the present invention is embodied in a novel apparatus and method for Supercritical Fluid Chromatography (SFC).

Figure 2:
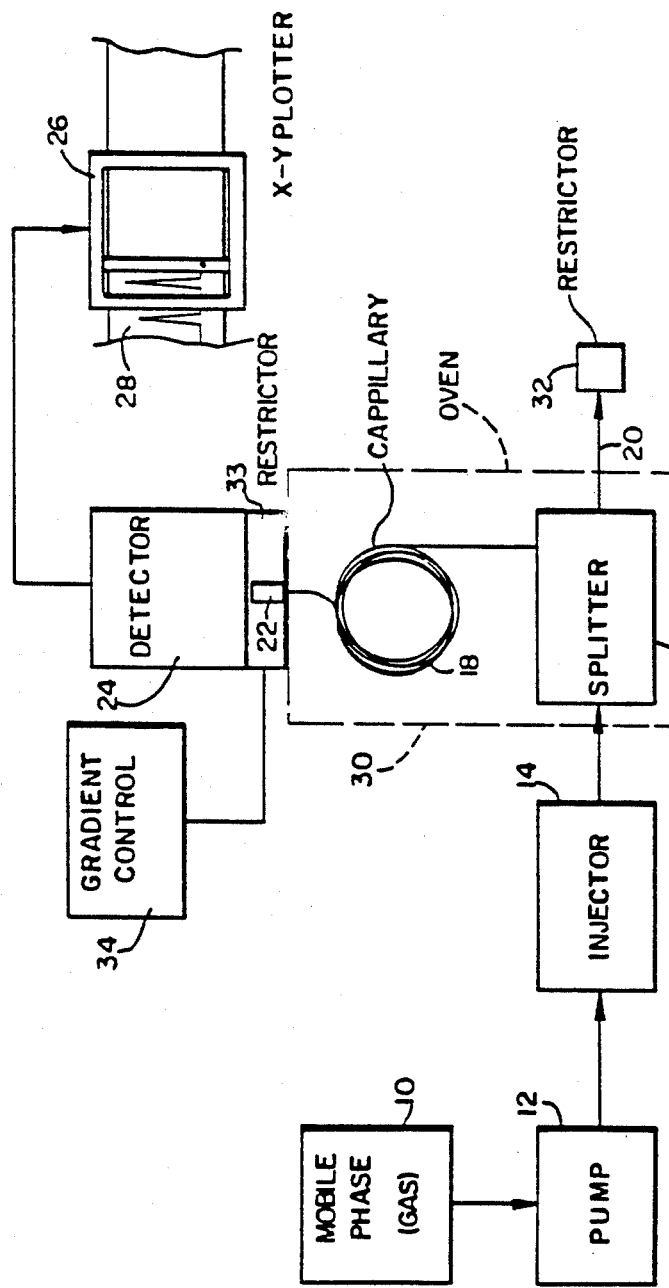
FIG. 2 is a diagrammatic view of a supercritical fluid chromatography system in accordance with the present invention.

As shown in FIG. 2, a mobile phase gas is supplied from a source 10 to pump 12. The mobile phase is provided by pump 12 under pressure through injector 14 to splitter 16. A sample (not shown) to be analyzed is injected into the mobile phase stream by injector 14. Pump 12, injector 14, splitter 16 and the means for interconnection are all known. For purposes of the present description, it is preferred that pump 12 be programmable so that mobile phase pressure can be fixed to preselected values and modified to increase pressure at various rates during a test run.

Splitter 16 provides a portion of the mobile phase/-sample combination to capillary 18 and the remaining to a non-analyzed output 20. The ratio between that portion provided to capillary 18 and that provided to output 20 is known as the split ratio. As is known, the split ratio is the ratio of flow into the capillary to flow into the non-analyzed output.

In a preferred embodiment, capillary 18 is 10 meters long and has an internal diameter of 50 microns. Since capillary SFC requires the mobile phase to be subjected to predetermined pressure conditions while in the capillary, it is known and preferred that the pressure in capillary 18 be controlled by pump 12.

Figure 1:
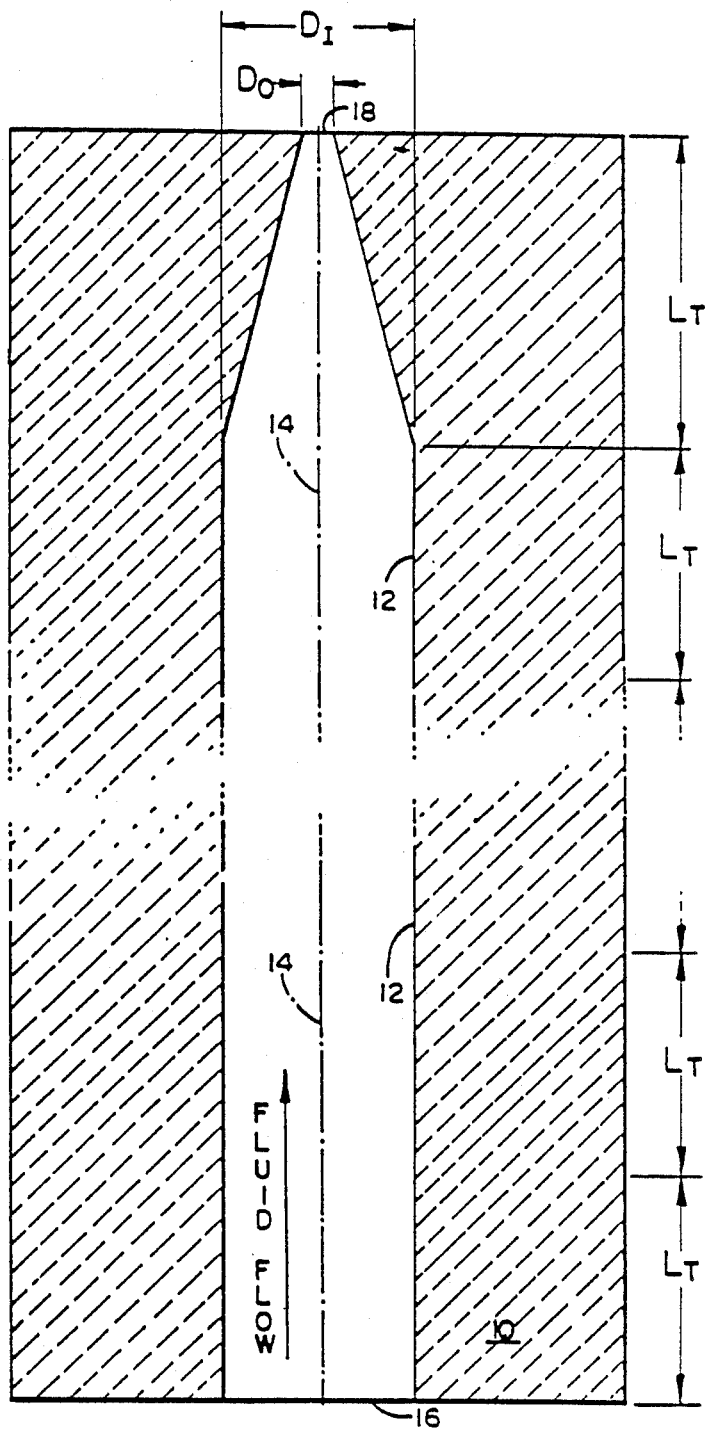
FIG. 1 is a section view of a capillary SFC restrictor.

Since pressure conditions are to be maintained in capillary 18 and since a gas chromatography detector is to be utilized, a restrictor 22 is attached in any known manner to the outlet end of capillary 18. It is preferred that restrictor 22 be a fused silica restrictor generally of the design shown in FIG. 1 having an internal diameter of less than 10 $\mu$m, a length of 1 cm and an outside diameter of about 300 $\mu$m. Restrictor 22 is also fixed in the base of detector 24. While detector 24 can be any known detector, for the purposes of the present description it is preferred that detector 24 be a gas chromatography Flame Ionization Detector (FID). The output of detector 24 in the preferred embodiment, is a voltage signal which is applied to the input of plotter 26. Plotter 26 creates a chart 28 over time of the detector output voltage. Such charts are known as chromatographs.

Since SFC requires the mobile phase to be heated to a temperature above its critical temperature, splitter 16, capillary 18 and restrictor 22 are placed within oven 30. Although the mobile phase fluid need be supercritical only in the column, i.e. only the capillary need be placed in the oven, I have chosen to place the splitter in the oven as well. For purposes of the present invention any commercially available oven can be utilized which is capable of maintaining the temperature of the mobile phase above its critical temperature. Since pressure is to be maintained in splitter 16 during operation, a second restrictor 32 is placed on the non-analyzed output 20.

As indicated previously, a need exists in SFC to heat the mobile fluid prior to detection which need is due primarily to adiabatic cooling. There is an additional need to heat the mobile phase in SFC. I have found that linear velocity of the mobile phase in capillary 18 can be controlled during programmed pressure operation utilizing the density and viscosity properties of the mobile phase within restrictor 22 by adjusting the temperature of the fluid within restrictor 22. The details of that invention can be found in my filed patent application now U.S. Pat. No. 4,845,985 entitled IMPROVED SUPERCRITICAL FLUID CHROMATOGRAPHY.

In the present invention I have resolved the problems involved in heating the mobile fluid in capillary SFC by a novel combination of restrictor design and a heated zone which heated zone serves to heat the mobile phase passing through the restrictor. In an alternative embodiment of the invention , more than one heated zone is used to subject the mobile fluid to a thermal gradient in the area prior to the outlet end of the restrictor.

Apparatus for subjecting the mobile fluid to either a single heated zone or to a thermal gradient formed from a plurality of zones is shown generally in FIG. 2 to include a heated zone member 33 mounted in heat transfer relationship with restrictor 22. The detailed structure of member 33 in the embodiment establishing a thermal gradient is shown and will be described in greater detail in regard to FIG. 3. The heating maintained by member 33 is regulated by controller 34.

Consider first the novel combination of restrictor design and a single heated zone. There has been a desire in the past to use the existing heater found in the base of certain gas chromatography detectors, such as FID's, to program restrictor temperature in SFC. However, simply using an existing heated zone to controllably change temperature is not adequate. I have found that the combination of heated zone and restrictor design, if not selected in accordance with the principles of the present invention, causes detection inefficiency due to solutes dropping out of solution. The overall objective in the present invention is to maintain the density of the mobile phase, as it passes through the restrictor, as close as possible to the density of the mobile phase in the column or capillary for as long as possible. Two factors will effect the mobile phase density in the restrictor, namely the mobile phase pressure (the restrictor is a pressure reduction device) and the mobile phase temperature. Converting these principles to terms of structural design, the taper length should be as short as possible and the heated zone should be as short as possible so as to maintain mobile phase pressure as long as possible and to not prematurely raise the temperature of the mobile fluid.

Taper length effects mobile phase density because this is the region where pressure reduction is occurring. If the taper length is long, for example in restrictors manufactured by a drawing process, pressure reduction occurs in a fashion such that density reduction takes place too soon. If solutes have not dropped out of solution within the tapered region as a result of pressure related density reduction, the probability is very high that such solutes will drop out when the mobile phase reaches a heated zone region, which will further reduce density. In order to minimize the effects of the tapered region in a restrictor, the taper length distance should be as short as possible. Ideally, the tapered region of a restrictor would comprise an opening of desired diameter formed in a two dimensional plane, i.e. the taper length would be zero. Shorter taper length will also serve to maintain the flow characteristics of the mobile phase more turbulent than laminar.

When combining a heated zone with a restrictor having the above described preferred characteristics, it is also preferred to have a heated zone which raises the temperature of the mobile phase as close to the outlet end of the restrictor as possible. Ideally, such heated zone would be coextensive with the ideal taper length, i.e. have zero length. Since such a heated zone is not possible, it will instead be preferred to provide a heated zone which has a minimum length. Consider the heated zone generated in FIG. 3 by thermal block 52. This heated zone has a length in which the mobile phase will be subjected to heat transfer. The length of the heated zone is approximately equal to the length of block 52 which is in intimate contact with tube 56, which in turn contains restrictor 22.

In designing a heated zone of minimal length, certain other considerations should be taken into account. Making intimate contact between heater and restrictor for maximum heat transfer efficiency to a tube less than 0.5 mm OD is difficult. Increasing restrictor OD to increase surface area and make intimate contact easier also increases wall thickness thereby insulation, at least partially defeating the objective of heat transfer. Increasing zone length allows for increasing heat transfer, but, excessive increases in length can result in excessive pre-heating which in turn will cause solutes to drop out of solution.

The shortness of the heated zone and maximum restrictor ID allowable is determined by constraints in heat transfer through the restrictor and into the fluid. If the restrictor is very short it will necessarily have a very small ID. Fluid might be in contact with it for only very short times. Even at column linear velocity of 10 cm/sec, contact time in a 1 cm long column linear is 1/10th sec. If the restrictor diameter is 1/10th column diameter, its volume and contact time are $20 \times 10^{-6}$ sec. Since velocity can increase with expansion as much as 500 times across the restrictor, contact time could drop to tens of microseconds or less.

In accordance with an alternative embodiment of the present invention, the previously described heated zone is established by subjecting the mobile fluid to a thermal gradient before the fluid exits the restrictor, which gradient is formed from at least two heated zones which may be thermally coupled. A thermal gradient is created by providing a first temperature zone in an area immediately prior to the outlet of the restrictor. Spaced upstream from and thermally connected to the first zone is a second temperature zone. As fluid passes through the second zone, the space between the first and second zones, and the first zone, it is subjected to a thermal gradient.

Figure 3:
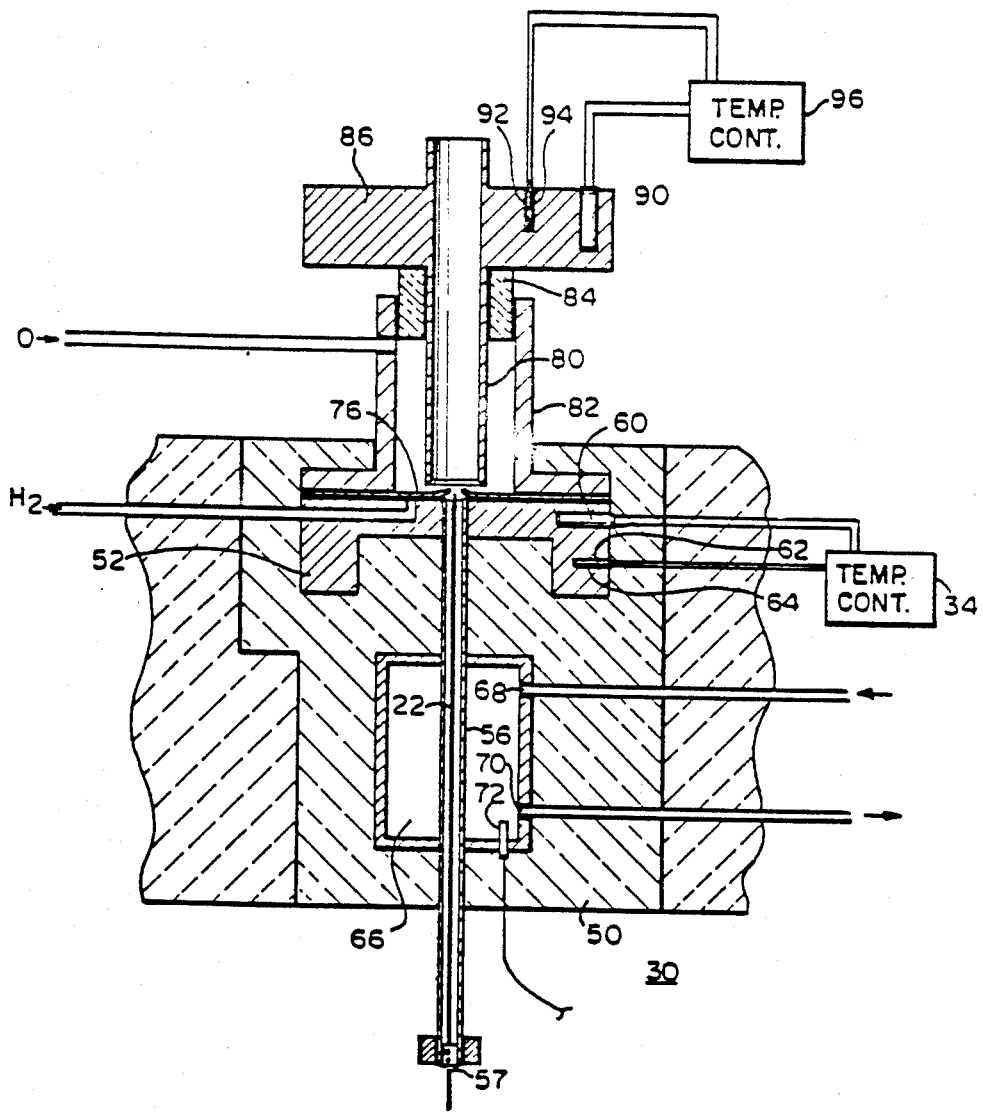
FIG. 3 is a section view of the base portion of a Flame Ionization Detector, modified for use with a capillary SFC system and incorporating one embodiment of the present invention.
Figure 4:
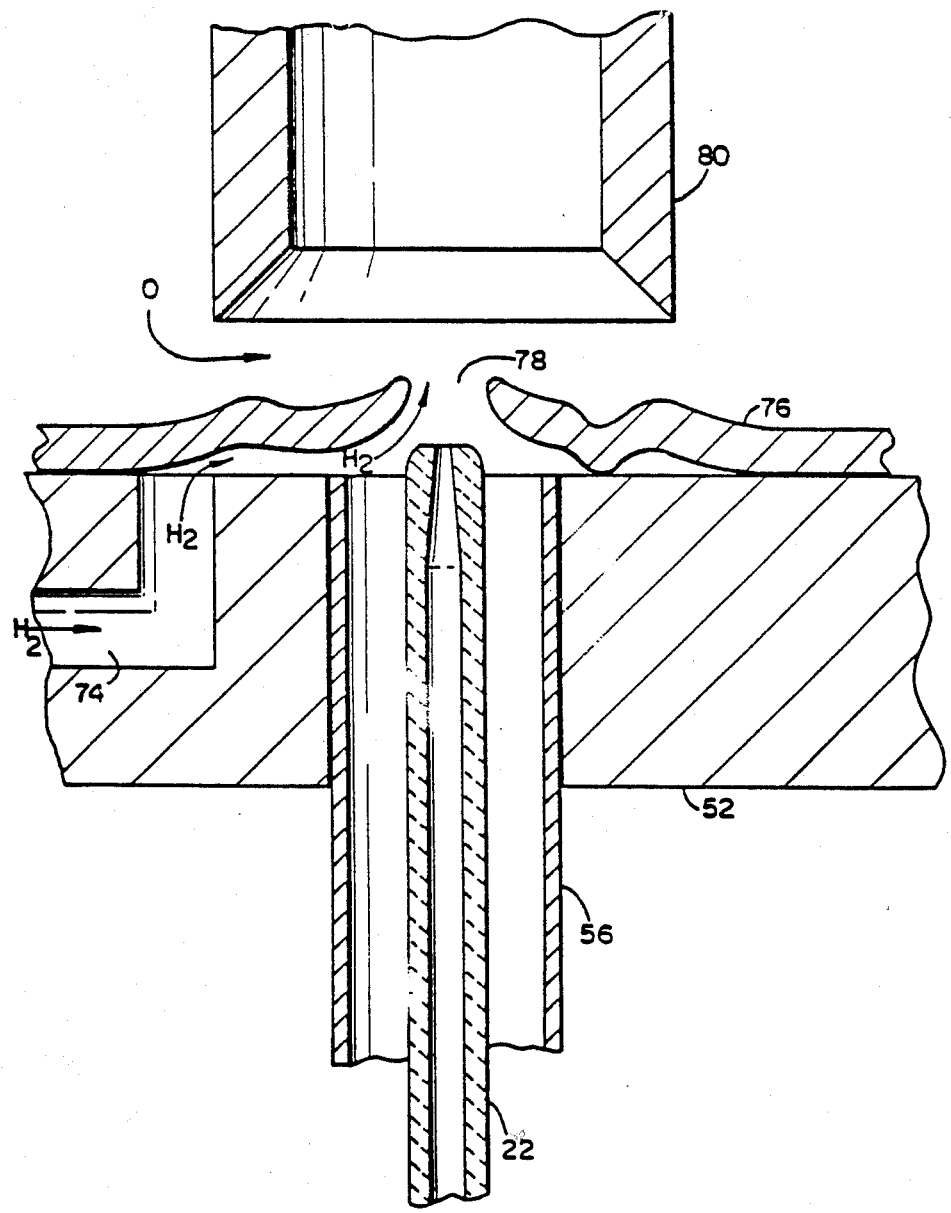
FIG. 4 is an enlarged view of a portion of the restrictor/detector/ structure illustrated in FIG. 3.

Consider now the structure shown in FIG. 3. Fixed in the wall insulation 50 of oven 30 is thermal block 52. Thermal block 52 is shown to have a centrally located bore. Tube 56 is positioned in the bore and is attached to block 52 by brazing or any other suitable method capable of producing a heat transfer relationship between block 52 and tube 56. Tube 56 may be formed from any thermally conductive material. The internal diameter of tube 56 is preferred to be on the order of 400 microns. The preferred outside diameter for tube 56 is approximately in the range from 0.0762 to 0.3175 cm with the preferred diameter nearer the lower end of the range to minimize heat transfer to fluid before it reaches the pressure drop region, i.e. the taper region, of the restrictor. Capillary 18 having a restrictor 22 attached to its outlet end is held within tube 56 by a press fit seal 57 or other suitable means. The preferred means for holding restrictor 22 within tube 56 is described in greater detail with regard to FIG. 5. It will be noted that the outlet end of restrictor 22 is approximately even with the end of tube 56 as shown in FIG. 4.

Heat is applied to block 52 by means of voltage controlled heater 60 inserted in a suitable bore. In order to assure that the temperature of block 52 is at a desired level, a temperature sensor 62 (for example a thermistor or a thermocouple) is inserted in a further bore 64. The voltage signal used to control heater 60 is generated by controller 34. Although not shown, the circuitry of controller 34 used to generate the voltage control signal can be of any known design capable of receiving the signal from sensor 62 and regulating the output of heater 60 such that a desired amounts of heat is transferred from block 52 through tube 56 through restrictor 22 to the fluid.

The axial length of tube 56 which is in intimate contact with block 52, i.e. the axial length of block 52 touching tube 56, defines a first temperature zone. It is preferred that this length be approximately in the range from 0.20 to 2 cm.

Spaced upstream from the first temperature zone is heat exchange chamber 66. As shown, tube 56 passes through chamber 66. Although it is not necessary to secure tube 56 to chamber 66, it is necessary for a fluid tight seal to be achieved at those spots where tube 56 enters and exits chamber 66. Chamber 66 may be made from any suitable material capable of preventing fluid introduced through port 68 to chamber 66 from escaping, except through port 70. Ports 68 and 70 are connected to a fluid source (not shown) by any suitable means. Fluid introduced to chamber 66 through port 68 is maintained at a desired temperature by any suitable means. In order to assure that the fluid temperature is maintained at the desired level, a sensor 72 is shown as being positioned to monitor such temperature. The axial length of tube 56 shown to be within chamber 66 defines the second temperature zone. In this embodiment it is preferred that the axial spacing between the top of chamber 66 and the bottom of block 52 along tube 56 is from approximately 0.5 to 5.0 cm.

Since it is preferred that an FID detection scheme be utilized, a bore 74 has been provided in block 52 for the introduction of hydrogen. Positioned immediately above block 52 is a jet plate 76 having a central opening 78. Positioned above and axially aligned with opening 78 is the detector chimney 80. Chimney 80 is typically formed from thermally conductive material and is held within cylinder 82 by insulation ring 84. Ring 84 serves to insulate cylinder 82 from the effects of thermal block 86, which is shown to be integrally formed with chimney 80. Such insulation is necessary since cylinder 82 may conduct and transfer thermal energy to block 52. Ring 84 also serves to create a fluid tight seal between chimney 80 and cylinder 82. Oxygen is introduced from a source (not shown) to the interior of cylinder 82 through port 88 by any suitable means.

Heat is applied to block 86 by means of voltage controlled heater 90 inserted in a suitable bore. In order to assure that the temperature of block 86 is at a desired level, a temperature sensor 92 (for example a thermistor or a thermocouple) is inserted in a further bore 94. The voltage signal used to control heater 90 is generated by temperature controller 96. Although not shown, the circuitry of controller 96 can be of any known design capable of receiving the signal from sensor 92 and regulating the output of heater 90 such that heat is transferred from block 86 to the interior walls of chimney 80. The primary purpose of block 86 is to raise the temperature of the walls of chimney 80 to prevent any water condensation which may occur as a result of the hydrogen/oxygen reaction.

Consider now the structure of FIGS. 3 and 4 during operation. As indicated previously, several reasons exist for heating the mobile fluid as it passes through the restrictor, for example to compensate for adiabatic cooling or to control linear velocity. However, heating the mobile fluid too soon or for too long, results in several problems, for example solute trapping or particle formation. By subjecting the mobile fluid to a thermal gradient problems can be overcome. The overall gradient zone allows for control of the temperature of mobile fluid until the fluid reaches the desired temperature just inside the restrictor taper region. The gradient zone extends from the bottom of chamber 66 to the top of block 52.

Consider the following example, in order to compensate for adiabatic of a carbon dioxide mobile phase, it is desired to heat the mobile phase prior to exiting the restrictor from 1.2 to 1.4 times the critical temperature. Controller 34 is arranged to generate a voltage control signal necessary for heater 60 to maintain the temperature of block 52 in the range of 1.2 to 1.4 times critical temperature. The temperature of fluid supplied to heat exchange chamber 66 is maintained at temperature. Usually the temperature of the fluid in chamber 66 will be maintained at oven temperature or lower. As will be appreciated, following a reading of the above, the tube 56 wall thickness, material selection for tube 56, spacing between the first and second zones and the temperatures within each zone will determine the actual thermal gradient applied to the mobile fluid.

Figure 5:
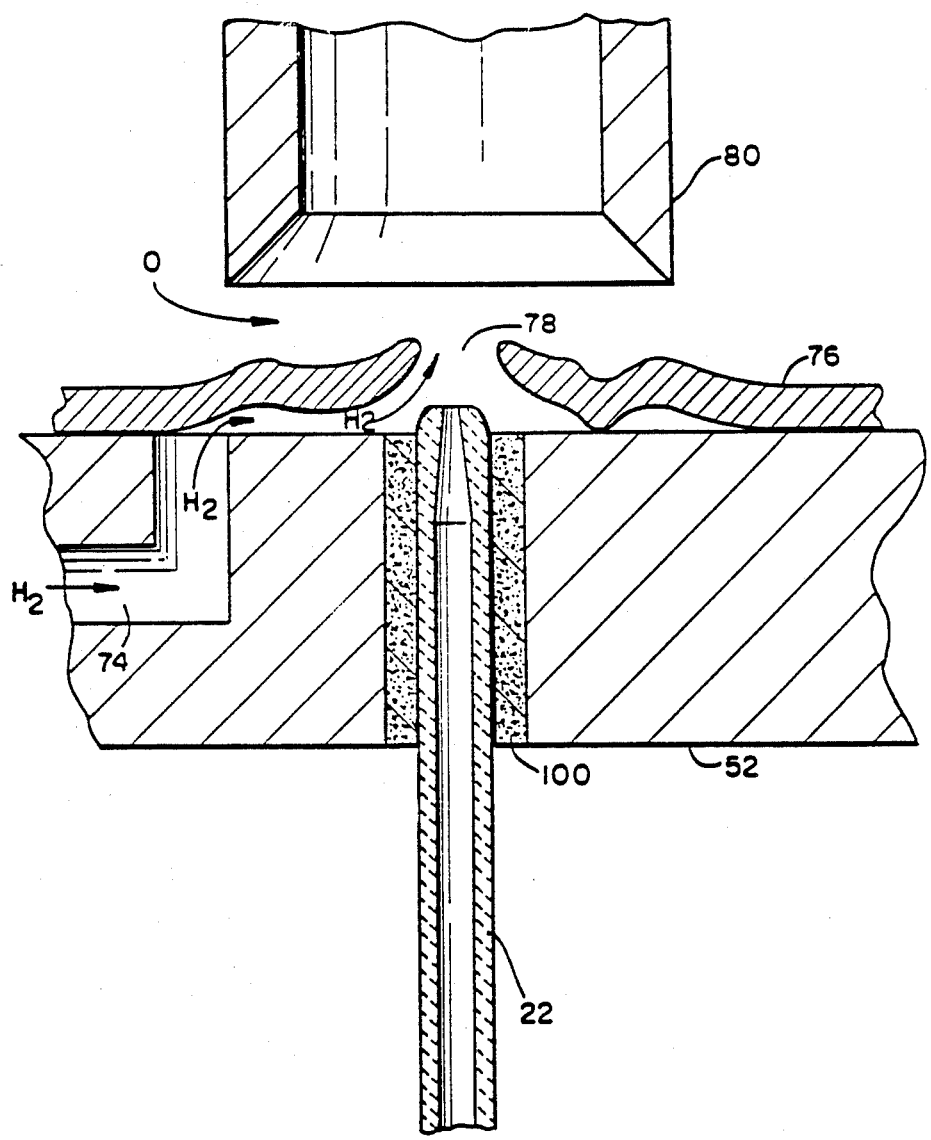
FIG. 5 is an alternative embodiment of the restrictor/detector structure shown in FIG. 4.

By subjecting the mobile fluid to a relatively short steep temperature gradient the previously mentioned problems can be overcome. Such an alternate embodiment of the present invention subjects the fluid to a single temperature zone which is no more than a few taper lengths $L_T$ long, i.e. preferably less than five (5) taper lengths. Such an alternative embodiment is shown in FIG. 5. In this embodiment, restrictor 22 is thermally conductively attached to heater block 52. Although such attachment can be accomplished via several different methods, one preferred method is potting. Potting is accomplished by filling the gap between restrictor 22 and block 52 with a metal filled epoxy and thereafter burning out the epoxy, leaving a porous sintered metal 100. If this method of attachment is to be utilized in connection with the embodiment shown in FIGS. 3 and 4, the metal filled epoxy is placed between restrictor 22 and the interior walls of tube 56.

When utilizing the FIG. 5 embodiment, it is within the scope of the invention to subject the fluid passing through the restrictor to a single temperature zone, defined by a length $L_z$, which is equal to the axial length of block 52 in contact with sintered metal 100. It is preferred that the length $L_z$ be a multiple of the taper length of restrictor 22 and that such multiple be 5 or less. The exact length is selected by determining that length which is just long enough to transfer sufficient heat to the fluid to raise or maintain its temperature at a desired level. Such length may be determined for only raising or maintaining the temperature at a single level or over a range of levels. If a range is desired, it will be necessary to ensure that the temperature zone length at both the highest and lowest levels is sufficient to maintain the fluid at those temperatures and is not so long as to cause solutes to drop out of solution.

In utilizing the embodiment shown in FIG. 5, although not essential, one may still want to incorporate a second heated zone as shown in FIG. 3. It is not necessary to thermally couple the two zones as long as the length of the first temperature zone is that length which is just long enough to transfer sufficient heat to the fluid to raise or maintain its temperature at a desired level. It should be understood that if incorporating the single temperature zone of FIG. 5, that the temperature controlling elements shown in FIG 3, i.e. block 52, heater 60 and sensor 62 can be utilized.

The embodiments described in connection with FIG. 5, assumes intimate contact of the heater with the exterior surface of the restrictor, i.e. potted mounting of the restrictor. If intimate contact does not exist, additional power will be required. Decreasing restrictor wall thickness or increasing length make adequate heat transfer more likely. The expansion will become more nearly isothermal than adiabatic, somewhat perturbing mass flow rate calculations, but this effect is not large.

Under certain temperature conditions, thermal decomposition may occur but since the chromatography has already been carried out before the solute reaches the restrictor the main concern should be whether thermal breakdown products are lost in the restrictor. If they can be transported to the detector without serious loss of mass an appropriate response can probably still be obtained. Of course some structural information on labile molecules would be lost.

If making the temperature zone length equal to the restrictor length, it should be kept in mind that very long restrictors drop virtually all of the system pressure inside the restrictor. This means fluid density inside the restrictor becomes very low, solutes tend to drop out of solution and stick to the walls or form particles which also can cause detector spiking. Long restrictors also tend to operate more isothermally than short adiabatic expansion devices. This will tend to further decrease density and viscosity at any point along the restrictor. Solute solubility will decrease, linear velocity will increase and so will solute volatility. Detector spiking due to solvent particles will likely decrease, but spiking due to solute particles may increase. Enhanced volatility and linear velocity should tend to deliver more of the solutes to the detector instead of the restrictor walls. This all suggests that such restrictors should be avoided whenever possible. The shortest, smallest ID restrictor yielding appropriate mass flow rates should always be used. This further means the heated zone length should match restrictor length or be no more than some small multiple of restrictor length.

While the invention has been described and illustrated with reference to specific embodiments, those skilled in the art will recognize that modification and variations may be made without departing from the principles of the invention as described herein above and set forth in the following claims.

I claim:

1. In a chromatographic analysis system, apparatus for maintaining the temperature of the mobile phase at a desired level, comprising in combination a restrictor, through which the mobile phase passes, said restrictor having a minimum taper length; and heated zone means for creating a temperature zone in an area immediately prior to the outlet end of said restrictor, said temperature zone having a length equal to the minimum length necessary to transfer sufficient heat to said mobile phase so that as said mobile phase passes through said zone, the temperature of said mobile phase is maintained at said desired level.

2. In a chromatographic analysis system, apparatus for raising the temperature of the mobile phase at a desired level, comprising in combination a restrictor, through which the mobile phase passes, said restrictor having a minimum taper length; and heated zone means for creating a temperature zone in an area immediately prior to the outlet end of said restrictor, said temperature zone having a length equal to the minimum length necessary to transfer sufficient heat to said mobile phase so that as said mobile phase passes through said zone, the temperature of said mobile phase is maintained at said desired level.

3. The apparatus of claim 2, wherein the desired temperature level for said mobile phase is a range of temperature levels and wherein said temperature zone length is equal to the length necessary to transfer sufficient heat to said mobile phase to any one of said temperature levels.

4. The apparatus of claim 2, wherein said restrictor has a taper length and wherein said length of said temperature zone is equal to a multiple of said taper length.

5. The apparatus of claim 4, wherein said multiple of said taper length is equal to 5.

6. The apparatus of claim 4, wherein said multiple of said taper length is less than 5.

7. In a chromatographic analysis system, apparatus for maintaining the density of the mobile phase at a desired level prior to detection, comprising in combination a restrictor, through which the mobile phase passes, said restrictor having a minimum taper length; and heated zone means for creating a temperature zone in an area immediately prior to the outlet end of said restrictor, said temperature zone having a length equal to the minimum length necessary to transfer sufficient heat to said mobile phase so that as said mobile phase passes through said zone, the density of said mobile phase is maintained at said desired level.

8. Apparatus for causing the temperature of the mobile phase to be at a desired level in a chromatographic analysis system, said apparatus comprising a restrictor, through which the mobile phase passes, said restrictor having a minimum taper length, and temperature zone means for creating a temperature zone in an area immediately prior to the outlet end of said restrictor, said temperature zone having a length equal to the minimum length necessary to transfer sufficient heat in relation to said mobile phase so that as said mobile phase passes through said zone, the temperature of said mobile phase is at said desired level.

9. Apparatus for causing the temperature of the mobile phase to be at a desired level in a chromatographic analysis system, said apparatus comprising:
   a restrictor, through which the mobile phase passes, said restrictor having an inlet end and a minimum taper length; and
   temperature zone means for creating a temperature zone in an area immediately prior to the outlet end of said restrictor, said temperature zone having a length no longer than that length necessary to ensure that the density of said mobile phase at said inlet end does not drop more than fifty percent when said mobile phase passes out of said restrictor.

10. Apparatus for causing the temperature of the mobile phase to be at a desired level in a chromatographic analysis system, said apparatus comprising:
   a restrictor, through which the mobile phase passes, said restrictor having an inlet end and an outlet end; and
   temperature zone means for creating a temperature zone in an area immediately prior to the outlet end of said restrictor, said temperature zone having a length no longer than that length necessary to maintain the density of the mobile phase at a level which prevents solutes from dropping out of solution.

11. The apparatus of claim 10, wherein said temperature zone is of a length necessary to maintain the density of the mobile phase at a level which prevents all solutes from dropping out of solution.

12. Apparatus for causing the temperature of the mobile phase to be at a desired level in a chromatographic analysis system, said apparatus comprising:
   a restrictor, through which the mobile phase passes, said restrictor having an inlet end and an outlet end; and
   temperature zone means for creating a temperature zone in an area immediately prior to the outlet end of said restrictor, said temperature zone having a length no greater than 20 mm.

13. The apparatus of claim 12, wherein said temperature zone length is in the range from 2 to 20 mm.

14. The apparatus of claim 12, wherein said temperature zone length is less than 2 mm.

* * * * *